United States Patent [19]

Fest et al.

[11] Patent Number: 4,910,221

[45] Date of Patent: Mar. 20, 1990

[54] PESTICIDAL ALPHA-METHYLSULPHONYL-BENZALDOXIME DERIVATIVES

[75] Inventors: Christa Fest, Wuppertal; Gerd Hänssler, Leverkusen; Wilhelm Brandes, Leichlingen, all of Fed. Rep. of Germany

[73] Assignee: Bayer Aktiengesellschaft, Leverkusen, Fed. Rep. of Germany

[21] Appl. No.: 179,153

[22] Filed: Apr. 8, 1988

[30] Foreign Application Priority Data

Apr. 14, 1987 [DE] Fed. Rep. of Germany ....... 3712631

[51] Int. Cl.$^4$ ................... C07C 147/06; A01N 41/10; A01N 47/06
[52] U.S. Cl. ...................... 514/512; 71/90; 71/103; 514/448; 514/508; 514/640; 549/71; 558/262; 564/254
[58] Field of Search ............. 549/71; 564/254; 514/640, 508, 512, 448; 558/262; 71/103, 90

[56] References Cited

U.S. PATENT DOCUMENTS

| | | | |
|---|---|---|---|
| 3,624,091 | 11/1971 | Daum et al. | 558/262 X |
| 3,914,300 | 10/1975 | Haddock et al. | 558/262 X |
| 4,466,822 | 8/1984 | Martin | 564/300 |
| 4,475,945 | 10/1984 | Martin | 558/262 X |

FOREIGN PATENT DOCUMENTS 3708320 9/1988 Fed. Rep. of Germany ...... 564/254

*Primary Examiner*—Werren B. Lone
*Attorney, Agent, or Firm*—Sprung Horn Kramer & Woods

[57] ABSTRACT

Pesticidal novel α-methylsulphonyl-benzaldoxime derivatives of the formula

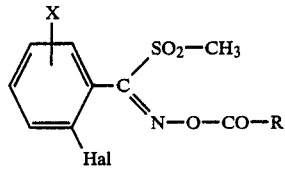

in which R represents alkyl, alkoxy, halogenoalkyl, halogenoalkoxy or alkenyloxy, aryl or aryloxy which is in each case optionally monosubstituted to polysubstituted by identical or different substituents, aralkyloxy which is optionally monosubstituted to polysubstituted in the aryl radical by identical or different substituents, cycloalkyloxy which is optionally monosubstituted to polysubstituted by identical or different substituents, or a heterocyclic ring which is optionally monosubstituted to polysubstituted by identical or different substituents, X represents hydrogen or halogen, and Hal represents halogen.

10 Claims, No Drawings

PESTICIDAL ALPHA-METHYLSULPHONYL-BENZALDOXIME DERIVATIVES

The present invention relates to new α-methylsulphonyl-benzaldoxime derivatives, a process for their preparation, and their use for combating pests, in particular fungi.

A number of aldoxime derivatives have already been disclosed. Thus, for example, arylsulphonylbenzaldoximes, such as α-phenylsulphonyl-2,6-dichloro-benzaldoxime, and their use as pesticides, above all their use in agents for combating stinking smut of wheat, have been disclosed (cf. Swiss Patent No. 423,350). In addition, α-(4-methylphenylsulphonyl)-benzaldoxime derivatives, such as, for example, α-(4-methylphenylsulphonyl)-2,6-dichlorobenzaldoxime (4-chloro-3-methylphenyl)-carbamate, have been disclosed for combating pests (cf. DE-OS (German Published Specification) No. 3,520,943.

New α-methylsulphonyl-benzaldoxime derivatives of the general formula (I)

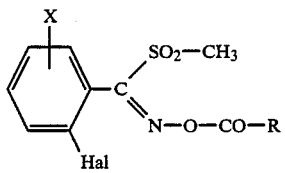

(I)

in which

R represents alkyl, alkoxy, halogenoalkyl, halogenoalkoxy or alkenyloxy, aryl or aryloxy which is in each case optionally monosubstituted to polysubstituted by identical or different substituents, aralkyloxy which is optionally monosubstituted to polysubstituted in the aryl radical by identical or different substituents, cycloalkyloxy which is optionally monosubtituted to polysubstituted by identical or different substituents, or a heterocyclic ring which is optionally monosubstituted to polysubstituted by identical or different substituents, X represents hydrogen or halogen, and Hal represents halogen, have been found.

It has furthermore been found that the α-methylsulphonyl-benzaldoxime derivatives of the formula (I)

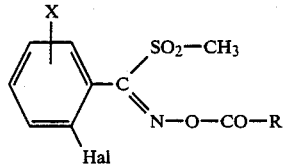

(I)

in which

R represents alkyl, alkoxy, halogenoalkyl, halogenoalkoxy or alkenyloxy, aryl or aryloxy which is in each case optionally monosubstituted to polysubstituted by identical or different substituents, aralkyloxy which is optionally monosubstituted to polysubstituted in the aryl radical by identical or different substituents, cycloalkyloxy which is optionally monosubstituted to polysubstituted by identical or different substituents, or a heterocyclic ring which is optionally monosubstituted to polysubstituted by identical or different substituents, X represents hydrogen or halogen, and Hal represents halogen, are obtained when α-methylsulphonyl-benzaldoximes of the general formula (II)

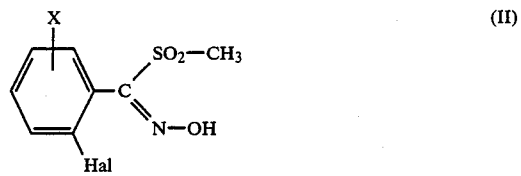

(II)

in which

X and Hal have the abovementioned meaning, are reacted with carbonyl compounds of the general formula (III)

$$X-CO-R \qquad (III)$$

in which

R has the abovementioned meanings and

X represents a halogen atom, preferably chlorine, or the —O—COR radical in which R has the abovementioned meaning, if appropriate in the presence of a solvent or diluent and if appropriate in the presence of an acid-binding agent.

The α-methylsulphonyl-benzaldoxime derivatives of the formula (I) according to the invention have strong biological properties, above all fungicidal properties.

Surprisingly, the compounds according to the invention at the same time exhibit a considerably greater activity, above all a fungicidal activity, than the compounds known from the prior art which are structurally similar compounds with a very similar mode of action.

The compounds of the formula (I) according to the invention can be produced as syn or anti isomers or as mixtures thereof in various ratios. The invention relates both to the pure isomers and to the isomeric mixtures.

The alkyl radicals in R and the alkyl parts in the alkoxy radicals in R may be straight-chain or branched and preferably contain 1 to 6, in particular, 1 to 4, carbon atoms in each case. Examples which may be mentioned are: methyl, ethyl, n-propyl, iso-propyl, n-butyl, sec.-butyl, iso-butyl, tert.-butyl, n-pentyl, iso-pentyl, sec.-pentyl, n-hexyl sec.-hexyl, methoxy, ethoxy, n-propoxy, iso-propoxy, n-butoxy, iso-butoxy, sec.-butoxy, tert.-butoxy, n-pentoxy, iso-pentoxy, sec.-pentoxy, n-hexoxy and sec.-hexoxy.

The alkenyloxy radical in R preferably contains 2 to 6, in particular 2 to 5, particularly preferably 2 or 3, carbon atoms. Examples which may be mentioned are: vinyl, allyl, propen-1-yl, butenyl and pentenyl.

The halogenoalkyl parts in R in the halogenoalkyl and halogenoalkoxy radicals preferably contain 1 to 6, in particular 1 to 4, particularly preferably 1 or 2, carbon atoms and preferably 1 to 9, in particular 1 to 5, particularly preferably 1 to 4, identical or different halogen atoms in each case. Examples which may be mentioned are: monochloromethyl, trichloromethyl, trifluoromethyl, dichlorofluoromethyl, trichloroethyl, tetrachloroethyl, trichloromethoxy, trichloroethoxy and tetrachloroethoxy.

Halogen, also in the radicals, such as halogenoalkyl and halogenoalkoxy, or in the aryl substituents, etc., denotes fluorine, chlorine, bromine or iodine, in particular fluorine or chlorine, if not particularly defined elsewhere.

Aryl, also in the aryloxy radical in R, may represent an aromatic hydrocarbon radical having 6 to 10 carbon atoms. Examples which may be mentioned are phenyl and naphthyl. Phenyl is preferred.

Aralkyl in aralkoxy in R may represent a radical having 7 to 16 carbon atoms, where a straight-chain or branched alkyl radical ($C_1$ to $C_6$) may be substituted by an aromatic radical ($C_6$ to $C_{10}$). Examples which may be mentioned are benzyl, phenyl-ethyl and phenyl-propyl. Benzyl is preferred.

Cycloalkyl in cycloalkyloxy may represent a cyclic, preferably monocyclic, hydrocarbon radical having 5 to 7 carbon atoms. Examples which may be mentioned are cyclopentyl, cyclohexyl and cycloheptyl. Cyclopentyl and cyclohexyl are preferred.

A heterocyclic ring may represent a saturated, partially or completely unsaturated 5- to 8-membered ring, preferably a 5- or 6-membered ring, having 1 to 3, and preferably 1 or 2, in particular 1, hetero atom, hetero atoms which may be mentioned being sulphur, oxygen or nitrogen, in particular sulphur.

The aryl, aryloxy and aralkyloxy mentioned may be unsubstituted or substituted; suitable substituents are 1 to 5, preferably 1 to 3, substituents, particularly preferably 1 or 2 substituents, from the group comprising the lower alkyl groups having 1 to 4 carbon atoms (methyl, ethyl, propyl, isopropyl, butyl and isobutyl), the lower alkoxy groups having 1 to 4 carbon atoms (methoxy, ethoxy, propoxy, isopropoxy, butoxy and isobutoxy) or the halogens (fluorine, chlorine and bromine). Further substituents may be the nitro group and the acetyl group.

The cycloalkyloxy mentioned may be unsubstituted or substituted; suitable substituents are 1 to 5, preferably 1 to 3, particularly preferably 1 or 2 substituents, from the group comprising the lower alkyl groups having 1 to 4 carbon atoms (methyl, ethyl, propyl, i-propyl, n- and s-butyl, i-butyl and t-butyl).

The heterocyclic ring mentioned may be unsubstituted or substituted. Suitable substituents are 1 to 3, preferably 1, substituent from the group comprising the lower alkyls having 1 to 4 carbon atoms, such as those listed above.

The formula (I) provides a general definition of the α-methylsulphonyl-benzaldoxime derivatives according to the invention. Preferred compounds of the formula (I) are those in which R represents straight-chain or branched alky having 1 to 6 carbon atoms, straight-chain or branched alkoxy having 1 to 6 carbon atoms, halogenoalkyl or halogenoalkoxy in each case having 1 to 6 carbon atoms in the straight-chain or branched halogenoalkyl radical and 1 to 9 identical or different halogen atoms, straight-chain or branched alkenyloxy having 2 to 6 carbon atoms, aryl or aryloxy having 6 to 10 carbon atoms which is unsubstituted or in each case monosubstituted to pentasubstituted by straight-chain or branched alkyl having 1 to 4 carbon atoms, straight-chain or branched alkoxy having 1 to 4 carbon atoms, halogen, nitro and acetyl, the substituents being identical or different, aralkyloxy which has 6 to 10 carbon atoms in the aryl radical and 1 to 6 carbon atoms in the straight-chain or branched alkyl radical and which is unsubstituted or monosubstituted to pentasubstituted by straight-chain or branched alkyl or alkoxy in each case having 1 to 4 carbon atoms, halogen, nitro and acetyl, the substituents being identical or different, cycloalkyloxy which has 5 to 7 carbon atoms in the cycloalkyl part and which is unsubstituted or monosubstituted to pentasubstituted by identical or different, straight-chain or branched alkyl having 1 to 4 carbon atoms, or a saturated, partially or completely unsaturated heterocylic ring having 5 to 8 ring members which may contain 1 to 3 heteroatoms and which is unsubstituted or monosubstituted, disubstituted or tri-substituted by identical or different, straight-chain or branched alkyl having 1 to 4 carbon atoms;

X represents hydrogen or halogen, and

Hal represents halogen.

Particularly preferred compounds of the formula (I) are those in which

R represents straight-chain or branched alkyl having 1 to 4 carbon atoms, straight-chain or branched alkoxy having 1 to 4 carbon atoms, halogenoalkyl or halogenoalkoxy in each case having 1 to 4 carbon atoms in the straight-chain or branched halogenoalkyl or halogenoalkoxy radical and 1 to 5 identical or different halogen atoms, straight-chain or branched alkenyloxy having 2 to 5 carbon atoms, phenyl or phenoxy which is in each case unsubstituted or monosubstituted to pentasubstituted by straight-chain or branched alkyl having 1 to 3 carbon atoms, straight-chain or branched alkoxy having 1 to 3 carbon atoms, halogen, nitro and acetyl, the substituents being identical or different, benzyloxy, phenethyloxy or phenylpropyloxy which is in each case unsubstituted or monosubstituted, disubstituted or tri-substituted by straight-chain or branched alkyl or alkoxy in each case having 1 to 3 carbon atoms, halogen, nitro and acetyl, the substituents being identical or different, or cycloalkyloxy which has 5 to 7 carbon atoms in the cycloalkyl part and which is unsubstituted or monosubstituted, disubstituted or trisubstituted by identical or different, straight-chain or branched alkyl having 1 to 3 carbon atoms, or a saturated, partly saturated or unsaturated heterocyclic ring having 5 to 7 ring members which may contain 1 or 2 sulphur, nitrogen and/or oxygen atoms and which is unsubstituted or monosubstitued by straight-chain or branched alkyl having 1 to 3 carbon atoms;

X represents hydrogen or halogen, and

Hal represents halogen.

Very particularly preferred compounds of the formula (I) are those in which

R represents straight-chain or branched alkyl having 1 to 4 carbon atoms, straight-chain or branched alkoxy having 1 to 4 carbon atoms, halogenoalkyl or halogenoalkoxy in each case having 1 or 2 carbon atoms in the straight-chain or branched halogenoalkyl or halogenoalkoxy radical and 1 to 4 identical or different halogen atoms, straight-chain or branched alkenyloxy having 2 or 3 carbon atoms, phenyl or phenoxy which is in each case unsubstituted or monosubstituted or disubstituted by alkyl having 1 or 2 carbon atoms, alkoxy having 1 or 2 carbon atoms, halogen, nitro and acetyl, the substituents being identical or different, benzyl which is unsubstituted or monosubstituted, disubstituted or trisubstituted by alkyl or alkoxy in each case having 1 or 2 carbon atoms or halogen, the substituents being identical or different, cycloalkyloxy which has 5 or 6 carbon atoms in the cycloalkyl part and which is unsubstituted or monosubstituted, disubstituted or trisubstituted by identical or different alkyl having 1 or 2 carbon atoms, or an unsaturated heterocyclic ring having 5 or 6 ring members which may contain a nitrogen or a sulphur atom and which is unsubstituted or monosubstituted or disubstituted by identical or different alkyl having 1 or 2 carbon atoms;

X represents hydrogen or halogen, and

Hal represents halogen.

Compounds of the formula (I) which may be mentioned in particular are those in which R represents methyl, ethyl, methoxy, ethoxy, n-propoxy, iso-propoxy, iso-butoxy, allyloxy, 2,2,2-trichloroethoxy, benzyloxy, chloromethyl, phenyl, 2,6-dichlorophenyl, 2,4-dichlorophenyl, phenoxy, thienyl or cyclohexyloxy, X represents hydrogen, fluorine or chlorine, and Hal represents fluorine or chlorine.

If 2,6-difluoro-α-(4-methylsulphonyl)-benzaldoxime and acetic anhydride are used as starting compounds, the course of the reaction of the process according to the invention may be represented by the following reaction equation:

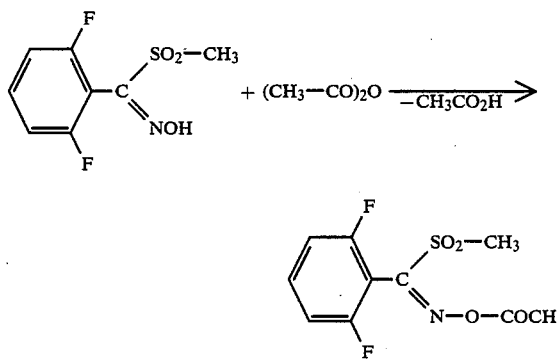

The α-methylsulphonyl-benzaldoximes of the general formula (II) required as starting materials for carrying out the process according to the invention are new. The new compounds can be prepared by analogous processes, for example by the process described in Swiss Patent No. 423,350 in Example VII, by reacting α-halogeno-benzaldoximes of the formula (IV)

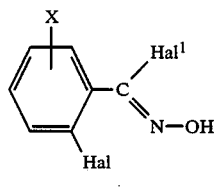

in which

X and Hal have the abovementioned meaning, and

Hal¹ represents halogen, preferably chlorine, with methanesulphinic acids of the formula (V)

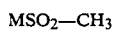

in which

M represents hydrogen or an alkali metal equivalent, if appropriate in the presence of a solvent and if appropriate in the presence of an acid acceptor.

The compounds of the formula (II) are described in application Ser. No. 179,094 filed Apr. 8, 1988, now U.S. Pat. No. 4,859,239 corresponding to German Application No. P 37 12 632.6.

The sulphinic acids are known compounds.

The formula (III) provides a definition of the carbonyl compounds furthermore required as starting materials. These are known compounds of organic chemistry.

The process according to the invention can be carried out, if appropriate, in the presence of a solvent or diluent. Suitable as such are, in principle, all inert organic solvents. Hydrocarbons, optionally chlorinated, such as, for example, benzene, toluene, xylene, methylene chloride, chloroform, carbon tetrachloride, chlorobenzene and dichlorobenzene, furthermore ethers, such as diethyl and dibutyl ether, glycol dimethyl ether and diglycol dimethyl ether, tetrahydrofuran and dioxane, furthermore ketones, such as acetone, methyl ethyl, methyl isopropyl and methyl isobutyl ketone, in addition esters, such as methyl and ethyl acetate, furthermore nitriles, such as, for example, acetonitrile and propionitrile, benzonitrile and glutarodinitrile, moreover amides, such as, for example, dimethylformamide, are preferably used.

Suitable acid-binding agents for the process according to the invention are conventional inorganic or organic acid binders. The following may be mentioned as such: for example tert. amines, such as triethylamine, pyridine, triethylenediamine, inter alia.

The reaction temperature in the process according to the invention may be varied within a relatively wide temperature range. In general, the process is carried out between 0° C. and 120° C., preferably between 20° C. and 70° C.

The reaction is usually carried out under atmospheric pressure. When carrying out the process according to the invention the compounds of the formula (ii) are generally introduced into a solvent with equimolar amounts of the acid binder, and the carbonyl compound of the formula (III) is added, preferably likewise in equimolar amounts. Work-up takes place by generally conventional methods.

A particular embodiment should be mentioned. If X denotes —O—COR, i.e. carboxylic anhydrides of the formula (III) are employed, the process is carried out without solvent using a large excess of the anhydride, which then simultaneously serves as starting material and solvent. Work-up likewise takes place by conventional methods.

The active compounds according to the invention have a strong biological action and can be employed in practice for combating undesired pests. The active compounds are suitable for use a pesticides, above all as fungicides.

Fungicidal agents in plant protection are employed for combating Plasmodiophoromycetes, Oomycetes, Chytridiomycetes, Zygomcetes, Ascomycetes, Basidiomycetes and Deuteromycetes.

Bactericidal agents are employed in plant protection for combating Pseudomonadaceae, Rhizobiaceae, Enterobacteriaceae, Some causitive organisms of fungal and bacterial Corynebacteriaeae and Streptomycetaceae. diseases which come under the generic names listed above may be mentioned as examples, but not by way of limitation: Xanthomonas species, such as, for example, *Xanthomonas campestris* pv. *oryzae;* Pseudomonas species, such as, for example, *Pseudomonas syringae* pv. *Lachrymans;* Erwinia species, such as, for example, *Erwinia amylovora;* Pythium species, such as, for example, *Pythium ultimum;* Phytophthora species, such as, for example, *Phytophthora infestans;* Pseudoperonospora species, such as, for example, *Pseudoperonospora humuli* or *Pseudoperonospora cubensis;* Plasmopara species, such as, for example, *Plasmopara viticola;* Peronospora species, such as, for example, *Peronospora pisi* or *P. brassicae;*

Erysiphe species, such as, for example, *Erysiphe graminis;* Sphaerotheca species, such as, for example, *Sphaerotheca fuliginea;* Podosphaera species, such as, for example, *Podosphaera leucotricha;* Venturia species, such as, for example, *Venturia inaequalis;* Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus;* Puccinia species, such as, for example, *Puccinia recondita;* Tilletia species, such as, for example, *Tilletia caries;* Ustilago species, such as, for example, *Ustilago nuda* or *Ustilago avenae;* Pellicularia species, such as, for example, *Pellicularia sasakii;* Pyricularia species, such as, for example, *Pyricularia oryzae;* Fusarium species, such as, for example, *Fusarium culmorum;* Botrytis species, such as, for example, *Botrytis cinerea;* Septoria species, such as, for example, *Septoria nodorum;* Leptosphaeria species, such as, for example, *Leptosphaeria nodorum;* Cercospora species, such as, for example, *Cercospora canescens;* Alternaria species, such as, for example, *Alternaria brassicae* and Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

The compounds of the formula (I) according to the invention exhibit a particularly good action against pathogens of fruit diseases caused, for example, by Venturia species, and rice diseases, caused by Pyricularia species, and the good Oomycetes action and the in vitro action against bacteria may furthermore be mentioned.

At appropriate concentrations, the substances according to the invention also exhibit herbicidal actions.

USE EXAMPLES

In the following examples, the compounds shown below were employed as comparison substances:

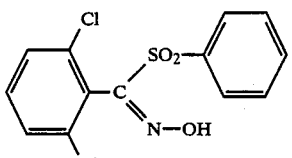

α-Benzosulphonyl-2,6-dichlorobenzaldoxime (known from Swiss 423,350; Example VII),

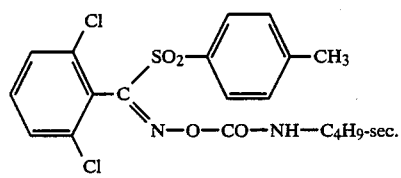

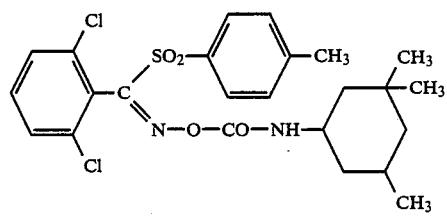

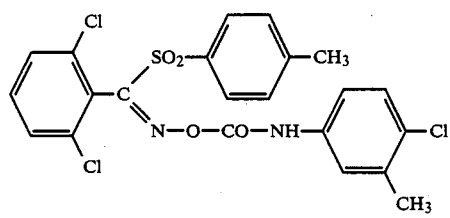

and

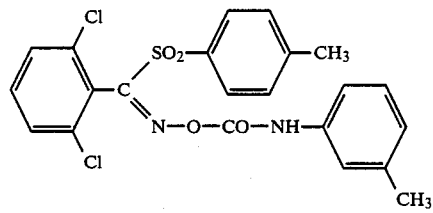

(B–E known from DE-OS (German Published Specification) 3,520,943).

EXAMPLE A

Pyricularia test (rice)/protective

Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

In this test, for example, the compounds according to Preparation Examples 1, 4, 2 and 3 exhibit a clearly superior activity compared to the prior art compared to (A), (B) and (C).

EXAMPLE B

Venturia test (apple)/protective

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (Venturia inaequalis) and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, for example, the compounds according to Preparation Examples 2 and 4 exhibit a clearly superior activity compared to the prior art compared to (A), (D) and (E).

Preparation Examples

EXAMPLE 1

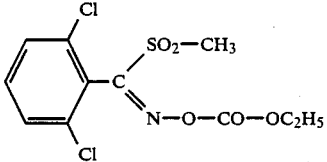

10 g (0.037 mol) of α-methylsulphonyl-2,6-dichlorobenzaldoxime are dissolved in 150 ml of acetonitrile, and 5.2 ml (0.037 mol) of triethylamine are added. 4 g (0.037 mol) of ethyl chloroformate are added at room temperature. The reaction proceeds slightly exothermically. The reaction mixture is kept at room temperature overnight, then poured into about 750 ml of ice water and extracted by stirring, and the solid is filtered off under suction, washed and dried. The product is subsequently stirred with isopropanol, filtered off under suction, washed with petroleum ether and dried.

10.6 g (84% of theory) of α-methylsulphonyl-2,6-chlorobenzaldoxime O-ethylcarbonate of melting point 169° C. are obtained.

The compounds of the formula (I)

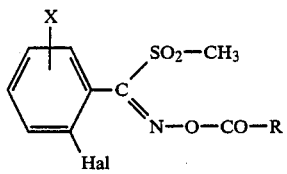
(I)

are prepared analogously:

| Example No. | X | Hal | R | Physical constants [Melting point °C.] |
|---|---|---|---|---|
| 2 | 2-Cl | Cl | —OCH$_2$—CH=CH$_2$ | 119 |
| 3 | 2-Cl | Cl | —OCH$_2$—CCl$_3$ | 153 |
| 4 | 2-F | F | —OC$_2$H$_5$ | 110 |
| 5 | 2-Cl | Cl | —CH$_3$ | 115 |
| 6 | 2-Cl | Cl | —OCH$_3$ | 170 |
| 7 | 2-Cl | Cl | —OC$_4$H$_9$-i | 75 |
| 8 | 2-Cl | Cl | —OCH$_2$—C$_6$H$_5$ | 138 |
| 9 | 2-Cl | F | —OCH$_3$ | 154 |
| 10 | 2-Cl | F | —OC$_2$H$_5$ | 113 |
| 11 | 2-Cl | F | —OCH$_2$—CH=CH$_2$ | 76 |
| 12 | 2-Cl | F | —OC$_4$H$_9$-i | 63 |
| 13 | 2-Cl | F | —OCH$_2$CCl$_3$ | 112 |
| 14 | 2-Cl | F | —OCH$_2$—C$_6$H$_5$ | 111 |

Preparation of the precursors

EXAMPLE 1A:

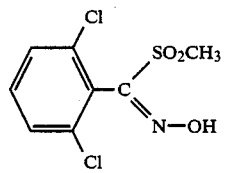

45 g (0.2 mol) of α-chloro-2,6-dichlorobenzaldoxime are dissolved in 200 ml of methanol, and 22.5 g (0.2 mol) of sodium S-methyl sulphite are added. The reaction proceeds exothermically. The reaction mixture is stirred overnight at room temperature. It is subsequently poured into about 1 liter of ice water and extracted by stirring, and the solid is filtered off with suction, washed and dried. After recrystallization from isopropanol, 35.5 g (66% of theory) of α-methylsulphonyl-2,6-dichlorobenzaldoxime of melting point 193° C. are obtained. The compounds of the formula (II)

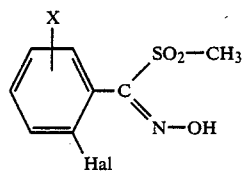
(II)

are prepared analogously:

| Example No. | X | Hal | Physical constants [Melting point 0° C.] |
|---|---|---|---|
| 2A | H | Cl | 161 |
| 3A | 2-F | F | 153 |
| 4A | 2-Cl | F | 168 |

The α-chloro-2,6-dichlorobenzaldoxime required for the preparation of example 1A can be prepared, for example, analogously to the instructions in Swiss No. 423,350 (Example II):

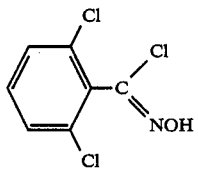

Chlorine was passed into a suspension of 19 parts by weight of 2,6-dichlorobenzaldoxime in 200 parts by volume of carbon tetrachloride until virtually all the oxime had dissolved. The temperature of the reaction during this was kept below 15° C. The green solution obtained was evacuated in order to remove excess chlorine and a volatile substance, presumably a nitrosyl chloride. 21.2 parts by weight of residue were partially brought to crystallization on standing. The residue was dissolved in 100 volumes of hot 60°/80° petroleum ether. On cooling, 10 parts by weight of flakes were obtained. Melting point 89°–94°. These flakes were filtered off and recrystallized from 60°/80° C. petroleum ether, and then had a melting point of 93.5° to 94.5°.

| Analysis: | | |
|---|---|---|
| Found: | C 37.1% | H 1.9% |
| Required for C$_7$H$_4$ONCl$_3$ | C 37.4% | H 1.8% |

A yellow oil was isolated from the mother liquor and identified as 2,6-dichlorobenzal dichloride.

It will be understood that the specification and examples are illustrative but not limitative of the present invention and that other embodiments within the spirit and scope of the invention will suggest themselves to those skilled in the art.

We claim:

1. An α-methylsulphonyl-benzaldoxime derivative of the formula

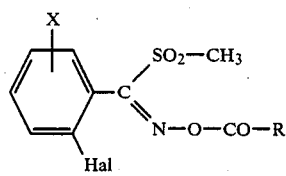

in which
R represents straight-chain or branched alkyl having 1 to 6 carbon atoms, straight-chain or branched alkoxy having 1 to 6 carbon atoms, halogenoalkyl or halogenoalkoxy in each case having 1 to 6 carbon atoms in the straight-chain or branched halogenoalkyl radical and 1 to 9 identical or different halogen atoms, straight-chain or branched alkenyloxy having 2 to 6 carbon atoms, aryl or aryloxy having 6 to 10 carbon atoms which is unsubstituted or in each case monosubstituted to pentasubstituted by straight-chain or branched alkyl having 1 to 4 carbon atoms, straight-chain or branched alkoxy having 1 to 4 carbon atoms, halogen, nitro and acetyl, the substituents being identical or different, aralkyloxy which has 6 to 10 carbon atoms in the aryl radical and 1 to 6 carbon atoms in the straight-chain or branched alkyl radical and which is unsubstituted or monosubstituted to pentasubstituted by straight-chain or branched alkyl or alkoxy in each case having 1 to 4 carbon atoms, halogen, nitro and acetyl, the substituents being identical or different, cycloalkyloxy which has 5 to 7 carbon atoms in the cycloalkyl part and which is unsubstituted or monsubstituted to pentasubstituted by identical or different, straight-chain or branched alkyl having 1 to 4 carbon atoms, or thienyl, X represents hydrogen or halogen, and Hal represents halogen.

2. An α-methylsulphonyl-benzaldoxime derivative according to claim 1, in which

R represents straight-chain or branched alkyl having 1 to 4 carbon atoms, straight-chain or branched alkoxy having 1 to 4 carbon atoms, halogenoalkyl or halogenoalkoxy in each case having 1 to 4 carbon atoms in the straight-chain or branched halogenoalkyl radical and 1 to 5 identical or different halogen atoms, straight-chain or branched alkenyloxy having 2 to 5 carbon atoms, phenyl or phenoxy which is in each case unsubstituted or monosubstituted to pentasubstituted by straight-chain or branched alkyl having 1 to 3 carbon atoms, straight-chain or branched alkoxy having 1 to 3 carbon atoms, halogen, nitro and acetyl, the substituents being identical or different, benzyloxy, phenethyloxy or phenylpropyloxy which is in each case unsubstituted or monosubstituted, disubstituted or trisubstituted by straight-chain or branched alkyl or alkoxy in each case having 1 to 3 carbon atoms, halogen, nitro and acetyl, the substituents being identical or different, or cycloalkyloxy which has 5 to 7 carbon atoms in the cycloalkyl part and which is unsubstituted or monosubstituted, disubstituted or trisubstituted by identical of different, straight-chain or branched alkyl having 1 to 3 carbon atoms, or thienyl.

3. An α-methylsulphonyl-benzaldoxime derivative according to claim 1, in which

R represents straight-chain or branched alkyl having 1 to 4 carbon atoms, straight-chain or branched alkoxy having 1 to 4 carbon atoms, halogenoalkyl or halogenoalkoxy in each case having 1 or 2 carbon atoms in the straight-chain or branched halogenoalkyl or halogenoalkoxy radical and 1 to 4 identical or different halogen atoms, straight-chain or branched alkenyloxy having 2 or 3 carbon atoms, phenyl or phenoxy which is in each case unsubstituted or monosubstituted or disubstituted by alkyl having 1 or 2 carbon atoms, alkoxy having 1 or 2 carbon atoms, halogen, nitro and acetyl, the substituents being identical or different, benzyl which is unsubstituted or monosubstituted, disubstituted or trisubstituted by alkyl or alkoxy in each case having 1 or 2 carbon atoms or halogen, the substituents being identical or different, cycloalkyloxy which has 5 or 6 carbon atoms in the cycloalkyl part and which is unsubstituted or monosubstituted, disubstituted or trisubstituted by identical or different alkyl having 1 or 2 carbon atoms, or thienyl.

4. An α-methylsulphonyl-benzaldoxime derivative according to claim 1, in which

R represents methyl, ethyl, methoxy, ethoxy, n-propoxy, iso-propoxy, iso-butoxy, allyloxy, 2,2,2-trichloroethoxy, benzyloxy, chloromethyl, phenyl, 2,6-dichlorophenyl, 2,4-dichlorophenyl, phenoxy, thienyl or cyclohexyloxy, X represents hydrogen, fluorine or chlorine, and Hal represents fluorine or chlorine.

5. A compound according to claim 1, wherein the compound is α-methylsulphonyl-2,6-chlorobenzaldoxime O-ethylcarbonate of the formula

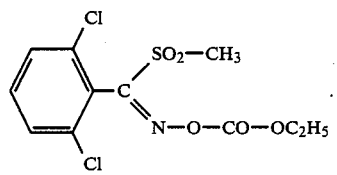

6. A compound according to claim 1, wherein the compound is α-methylsulphonyl-2,6-chlorobenzaldoxime O-allylcarbonate of the formula

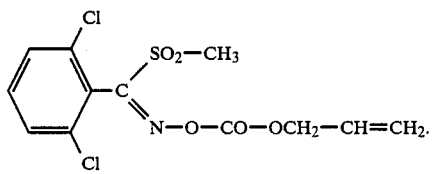

7. A compound according to claim 1, wherein the compound is α-methylsulphonyl-2,6-fluorobenzaldoxime O-ethylcarbonate of the formula

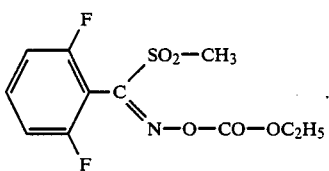

8. A pesticidal composition comprising a pesticidally effective amount of a compound according to claim 1 and a diluent.

9. A method of combating pests which comprises applying to such pests or to a pest habitat a pesticidally effective amount of a compound according to claim 1.

10. The method according to claim 9, wherein the compound is

α-methylsulphonyl-2,6-chlorobenzaldoxime O-ethylcarbonate,

α-methylsulphonyl-2,6-chlorobenzaldoxime O-allylcarbonate, or

α-methylsulphonyl-2,6-fluorobenzaldoxime O-ethylcarbonate.

* * * * *